United States Patent [19]

White

[11] 4,418,229
[45] Nov. 29, 1983

[54] METHOD FOR PRODUCING FLUORONITROBENZENE COMPOUNDS

[75] Inventor: Carl R. White, St. Louis, Mo.

[73] Assignee: Mallinckrodt, Inc., St. Louis, Mo.

[21] Appl. No.: 254,357

[22] Filed: Apr. 15, 1981

[51] Int. Cl.$^3$ ............................................. C07C 79/12
[52] U.S. Cl. ..................................... 568/938; 568/937
[58] Field of Search ................................ 568/937, 938

[56] References Cited

U.S. PATENT DOCUMENTS

| | | | |
|---|---|---|---|
| 3,064,058 | 11/1962 | Duesel et al. | 568/937 |
| 3,240,824 | 3/1966 | Boudakian et al. | 568/937 |
| 3,992,432 | 11/1976 | Napier et al. | 260/465.1 |
| 4,069,262 | 1/1978 | Kunz | 568/937 |
| 4,140,719 | 2/1979 | Tull et al. | 564/417 |
| 4,164,517 | 8/1979 | Fuller | 568/938 |
| 4,226,811 | 10/1980 | Oeser et al. | 568/937 |
| 4,229,365 | 10/1980 | Oester et al. | 568/937 |
| 4,287,374 | 9/1981 | North | 568/937 |

FOREIGN PATENT DOCUMENTS 1469700  4/1975  United Kingdom .

OTHER PUBLICATIONS

G. C. Finger et al., *J. Am. Chem. Soc.* 78, 6034 (1956).

*Primary Examiner*—Leland A. Sebastian
*Attorney, Agent, or Firm*—Bernard, Rothwell & Brown

[57] ABSTRACT

A method for producing fluoronitrobenzene compounds by reacting chloronitrobenzene compounds with a fluoride salt in the presence of a quaternary ammonium salt phase-transfer catalyst, wherein the catalyst is added to the reaction mixture incrementally during the course of the reaction. The incremental addition of catalyst allows the use of elevated reaction temperatures which, although sometimes causing catalyst inactivation, result in yields and reaction rates which are improved over those of methods involving a single catalyst addition.

16 Claims, No Drawings

METHOD FOR PRODUCING FLUORONITROBENZENE COMPOUNDS

BACKGROUND OF THE INVENTION

The present invention relates to a method for producing fluoronitrobenzene compounds. Fluoronitrobenzene compounds such as 2-fluoronitrobenzene, 4-fluoronitrobenzene, and 2,4-difluoronitrobenzene, are useful as intermediates for the synthesis of various hebicidal compounds, dyes, and the like. Such compounds have been prepared from corresponding chloronitrobenzene compounds by so-called halogen exchange reactions, illustrated as follows:

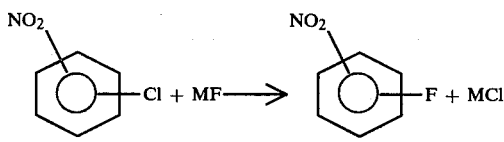

wherein MF represents an alkali metal fluoride salt. The reaction is generally conducted in an aprotic, polar, organic solvent, such as dimethylsulfoxide, dimethylformamide, tetramethylenesulfone, and the like.

Alkali metal fluoride salts are not soluble in such solvents, therefore, the reaction mixtures usually contain two phases, i.e., solid and liquid phases or two immiscible liquid phases. Finger, G. C., et al., *J. Am. Chem. Soc.*, 78, 6034 (1956) and Duesel, B. F., et al., U.S. Pat. No. 3,064,058 (Nov. 13, 1962), describe the reaction of chloronitrobenzene compounds with finely-divided, solid potassium fluoride in aprotic polar solvents to produce corresponding fluoronitrobenzene compounds. Boudakian, M. M., et al., U.S. Pat. No. 3,240,824 (Mar. 15, 1966), describe the reaction of o-chloronitrobenzene with solid potassium fluoride at elevated temperatures, without any solvent or diluents, to produce o-fluoronitrobenzene. Napier, D. R., et al., U.S. Pat. No. 3,992,432 (Nov. 16, 1976), describe a reaction involving two liquid phases. In that method, the inorganic fluoride salt is dissolved in an aqueous phase, and the chloronitrobenzene compound is dissolved in a water-immiscible, organic phase. The reaction is catalyzed by a quaternary salt, which reportedly transfers ions across the phase interface.

Quaternary salt phase-transfer catalysts have also been used in solid-liquid, two phase reactions. For instance, Kunz, R. A., U.S. Pat. No. 4,069,262 (Jan. 17, 1978), describes the production of 2-fluoronitrobenzene by reacting 2-chloronitrobenzene with finely-divided potassium fluoride in tetramethylenesulfone solvent using a macrocyclic ether (crown ether) or a quaternary ammonium halide catalyst, and Tull, R. J., et al., U.S. Pat. No. 4,140,719 (Feb. 20, 1979), describes the production of 5-chloro-2,4-difluoronitrobenzene by reaction 2,4,5-trichloronitrobenzene with solid potassium fluoride in an anhydrous organic solvent in the presence of a quaternary ammonium halide catalyst.

SUMMARY OF THE INVENTION

In accordance with the present invention, a method for producing fluoronitrobenzene compounds involves reacting a chloronitrobenzene compound with a fluoride salt in a substantially anhydrous, aprotic, polar organic solvent under halide-exchange conditions in the presence of a catalyzing amount of a quaternary ammonium salt phase-transfer catalyst, wherein the improvement comprises adding the phase-transfer catalyst to the reaction mixture incrementally during the course of the reaction.

The incremental addition of catalyst allows the use of an elevated reaction temperature which, although causing some inactivation of the catalyst, results in good reaction rates and yields. The procedure is also effective for the conservation of catalyst at such elevated temperatures.

DETAILED DESCRIPTION OF THE INVENTION

The halide-exchange reactions employed in the method of this invention have been found to proceed efficiently at elevated reaction temperatures. However, the quaternary ammonium salt catalysts utilized in the reaction are less stable at higher temperatures and have been found to decompose or lose their catalytic activity at elevated reaction temperatures. Although the catalyst might be present in catalyzing amounts at the beginning of the reaction at elevated temperatures, substantial depletion of the catalytic activity can occur before the reaction is complete. The later stages of the reaction therefore proceed inefficiently because of the lack of sufficient catalytic activity. On the other hand, if the reaction temperature is low, so as not to cause inactivation of the catalyst, the reaction proceeds slowly because insufficient activation energy is supplied.

It has now been found that in the conversion of chloronitrobenzene compounds to corresponding fluoronitrobenzene compounds using a quaternary ammonium salt phase-transfer catalyst at elevated temperatures, a high level of catalytic activity can be maintained by adding the catalyst to the reaction mixture incrementally during the course of the reaction. By this procedure, elevated reaction temperatures, which can cause deactivation of the catalyst, may be employed for optimum reaction rates and yields. Moreover, the reaction has been found to proceed at a good rate when only a part of the total catalyst heretofore employed is present initially, and additional catalyst is added incrementally to the reaction as it proceeds. By this procedure, the effective life of a given amount of catalyst is substantially extended, and yet the reaction rate is not significantly reduced from the relatively high rate obtained in the initial part of the reaction when virtually all of the catalyst is introduced at that time.

Thus, the halide-exchange conditions generally include elevated reaction temperatures, which are high enough to provide sufficient energy of activation for the reaction. Although such reaction temperatures might cause some catalyst inactivation, the temperature is preferably not so high as to cause rapid decay of catalytic activity or substantial decomposition of the reactants, the products, or the solvent. Although the reaction temperature may vary, depending upon the particular catalyst, solvent, and reactants used, generally, it can be from about 120° C. to about 220° C., and preferably ranges from about 150° C. to about 180° C.

Those skilled in the art will appreciate that a variety of equipment and techniques may be utilized in the method of the present invention, and the invention is not limited to any particular equipment or technique. The method is generally conducted by charging the reactants, solvent and an initial amount of catalyst into a reaction vessel which is equipped with agitating and heating means. The reaction vessel may also advantageously include a reflux condenser or other means for recovering solvent vapors and means for blanketing the reaction mixture with a dry gas, e.g. nitrogen. The reaction mixture is heated to the desired reaction temperature and agitated. Additional catalyst is added incrementally to the mixture either continuously or as separate, spaced-apart additions during the course of the reaction. The catalyst is conveniently added as a solution using the same solvent as that employed in the reaction. The rate at which catalyst is added and its concentration are adjusted, so that catalytic amounts of catalyst are present in the reaction mixture at times substantially throughout the reaction. The initial molar ratio of catalyst to chloronitrobenzene compound generally ranges from about 0.005:1 to about 0.1:1. Lower concentrations may not provide sufficient catalytic activity, and little appreciable benefit is derived from the use of higher catalyst concentrations. Preferred initial catalyst concentrations range from molar ratios of about 0.01:1 to about 0.03:1, most preferably about 0.02:1. After initiation of the reaction catalyst is generally added to the reaction mixture at a rate of from about 0.005 to about 0.1 mole per mole of chloronitrobenzene compound per hour, preferably from about 0.01 to about 0.03 mole per mole of chloronitrobenzene compound per hour. The catalyst may be added continuously or at intervals ranging up to about every two hours. Preferably, if the catalyst is added incrementally it will be added at intervals of about 1 hour or less, most preferably about every thirty minutes.

The halide-exchange reaction conditions employed in the present invention advantageously include substantially anhydrous reaction conditions. It is well known that the presence of water in such reaction can diminish yields and result in undesirable by-products. Various techniques may be used for dehydrating the reactants and solvent, such as vacuum drying, azeotropic distillation, chemical drying and the like. Azeotropic distillation, for example with benzene, has been used for drying all of the reactants and solvent; however, any convenient and operable technique may be employed. Because of the deleterious effect of water, the reaction mixture is preferably substantially devoid of water. Small amounts of water may be tolerated; however, a corresponding reduction in yield is generally experienced. Advantageously, the concentration of water in the reaction mixture is below about 5 wt. % and is preferably below about 1 wt. %, based on the weight of the reaction mixture.

The solvent for the catalyst, chloronitrobenzene compound, and fluoronitrobenzene compound is an aprotic, polar, organic solvent, which preferably has a relatively high boiling point, e.g., a boiling point above about 200° C. Lower boiling solvents may be used, however, pressure reactors may be required for their containment. Examples of reaction solvents include dimethylsulfoxide, sulfolane, bis(2-methoxyethyl)ether, bis[2-(2-methoxyethoxy)ethyl]ether, hexamethylphosphoramide, N-methylpyrolidinone, and dimethylformamide. Dimethylsulfoxide and hexamethylphosphoramide are preferred solvents, and dimethylsulfoxide is most preferred.

The phase-transfer catalyst employed in the present method is a quaternary ammonium salt which is soluble in the reaction solvent in an amount sufficient to catalyze the reaction. Such quaternary ammonium salts may be represented by the formula:

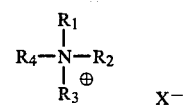

wherein each of $R_1-R_4$ is an alkyl group having up to about 30 carbon atoms, preferably up to about 20 carbon atoms, provided that at least one of $R_1-R_4$ is an alkyl group of from about 5 to about 30 carbon atoms, preferably from about 8 to about 20 carbon atoms. $X^-$ may be an anion which dissociates from the ammonium ion in the reaction solvent, e.g., chloride, fluoride, bromide, iodide, nitrate, bisulfate, and the like. $X^-$ is preferably a halide, especially chloride or fluoride. It has been found that lower molecular weight catalysts, i.e., those having a total number of carbon atoms less than about 16, are less stable under the conditions of the present method than the preferred catalysts of higher molecular weight having about 16 or more carbon atoms. A particularly preferred catalyst is sold under the trademark Aliquat ® 336 by McKerson Corp., Minneapolis, Minn. 55408, and is designated chemically as tricaprylmethylammonium chloride.

The fluoride ion is provided by an alkali metal fluoride salt which is generally present in an amount at least substantially stoichiometric to the chloronitrobenzene reactant. Preferred fluoride salts are potassium fluoride, rubidium fluoride, and cesium fluoride, and potassium fluoride is particularly preferred. The fluoride salt is advantageously finely divided, to provide a greater superficial surface area which is accessible to the catalyst and the chloronitrobenzene compound. Preferred concentrations of the fluoride salt range from about 1 to about 2 times the stoichiometric amount, most preferably from about 1.2 to about 1.6 times such amount. For example, in a method for producing a monofluoronitrobenzene compound, a preferred molar ratio of fluoride salt to chloronitrobenzene compound is about 1.5:1. Lower concentrations of fluoride salts can result in diminished reaction rates, and, although higher concentrations can be used, no appreciable benefit is generally realized therefrom.

The chloronitrobenzene compound used as the starting material in the present invention may be a compound in which a nitro group and a chloride atom occur on the same aromatic ring. The relative positions of the nitro and chloro substituents, and the presence of other subsituents on the ring can affect the reactivity of the starting compound. Generally, halogen exchange reactions involve compounds in which the chloride is in the ortho or para position with respect to the nitro group, and reactivity may increase when other electron-withdrawing groups are present on the ring. Compounds having chloro substituents in the meta as well as ortho and/or para positions may be used as starting materials, but usually only the chloro groups in the ortho and para positions will undergo halogen exchange. Accordingly, the method of this invention may be used for the synthesis of compounds such as 2-fluoronitrobenzene, 2-fluoro-3-chloronitrobenzene, 4-fluoronitrobenzene, 2,4-difluoronitrobenzene, 5-chloro-2,4-difluoronitrobenzene, and the like, from corresponding chloronitrobenzene compounds. The present method is particularly useful for the preparation of 4-fluoronitrobenzene from 4-chloronitrobenzene.

The reaction is generally allowed to proceed until substantially all of the chloronitrobenzene compound has been converted to the corresponding fluoronitrobenzene compound. A reaction time of from about 10 minutes to about 20 hours may typically be used, and the reaction will often be substantially complete after about 1 to about 6 hours. After the reaction is completed, the product can be recovered by any suitable procedure, such as extraction, distillation, steam distillation and the like. For some purposes, the purity of the crude reaction product, recovered as an organic phase after addition of water to reaction mixture, will be satisfactory.

The method of this invention has been found to produce fluoronitrobenzene compounds in good yields with little formation of by-products. The invention is further illustrated by the following examples, which are not intended to be limiting.

EXAMPLE I A three-necked, round bottom flask which was equipped with an overhead drive stirrer, thermometer and reflux condenser was thoroughly purged with nitrogen. While maintaining the nitrogen blanket, 4-chloronitrobenzene (200 g., 1.27 moles), azeotropically dried potassium fluoride (110 g, 1.90 moles) and dimethylsulfoxide (297 g, 3.81 moles) were charged to the reaction flask. To the reaction mixture was added 30 g of a solution which was prepared by adding azeotropically dried Aliquat ® 336 (50 g, 0.12 moles) to dimethylsulfoxide (100 g, 1.28 moles). The reaction mixture was heated to 170°–175° C. and maintained at this temperature for about four hours. Every thirty minutes after reaching 170°–175° C., 15 g of the Aliquat ® 336 solution was added for a total of seven additions. After four hours at 170°–175° C., the reaction mixture was cooled and treated with deionized water (1,200 ml). The organic layer was separated and assayed by HPLC to reveal a 90% yield of 4-fluoronitrobenzene.

EXAMPLE II p-Chloronitrobenzene (20.0 g, 0.127 mole), dimethylsulfoxide (19.8 g, 0.254 mole), anhydrous, finely divided potassium fluoride (8.8 g, 0.152 mole), and Aliquat ® 336 catalyst (1.0 g), were mixed in a round bottom flask equipped with a reflux condenser and a magnetic stirrer. The mixture was heated to 150°–155° C.; and additional Aliquat ® 336 catalyst was added in 0.5 g increments each half hour after reaching the reaction temperature. The progress of the reaction was monitored by periodically analyzing the reaction mixture by a gas chromatographic procedure using the following conditions: column packing: SE-30; column temperature: 170° C.; injection volume: 2ul; detector: flame ionization. The peak area of the p-fluoronitrobenzene product was compared to the peak area of the p-chloronitrobenzene reactant (expressed as area percentages), and the relative areas indicate the progress of the reaction, as a function of reaction time. Results of the analyses are listed in the following table:

| Reaction Time (Hours) | Area % p-CNB | Area % p-FNB |
| --- | --- | --- |
| 0.5 | 88.0 | 12.0 |
| 1.0 | 77.3 | 22.7 |
| 1.5 | 68.6 | 31.4 |
| 2.0 | 61.7 | 38.3 |
| 2.5 | 53.4 | 46.6 |
| 3.0 | 47.6 | 52.4 |

EXAMPLE III

The experiment of Example II was repeated in all essential details, except the reaction temperature was 170°–175° C. The results of the experiment are listed in the following table.

| Reaction Time (Hours) | Area % p-CNB | Area % p-FNB |
| --- | --- | --- |
| 0.5 | 63.0 | 37.0 |
| 1.0 | 53.1 | 46.9 |
| 1.5 | 37.9 | 62.1 |
| 2.0 | 30.8 | 69.2 |
| 2.5 | 24.5 | 75.5 |
| 3.0 | 21.1 | 78.9 |
| 3.5 | 18.1 | 81.9 |
| 5.5 | 12.9 | 87.1 |

EXAMPLE IV

The experiment of Example III was repeated in all essential details, except 11.0 g (0.91 mole) of potassium fluoride was used. The results of the experiment are listed in the following table:

| Reaction Time (Hours) | Area % p-CNB | Area % p-FNB |
| --- | --- | --- |
| 0.5 | 64.2 | 35.8 |
| 1.0 | 52.5 | 47.5 |
| 1.5 | 39.3 | 60.7 |
| 2.0 | 32.4 | 67.6 |
| 2.5 | 24.8 | 75.2 |
| 3.0 | 20.4 | 79.6 |
| 3.5 | 15.4 | 84.6 |

EXAMPLES V and VI

The experiment of Example IV was repeated in all essential details, except the concentration of the dimethylsulfoxide solvent was varied. In Example V, 24.8 g (0.318 mole) of dimethylsulfoxide was used, and in Example VI, 29.7 g (0.381 mole) of dimethylsulfoxide was used. The results of the experiments are listed in the following table:

| Reaction Time (Hours) | Area % p-CNB | | Area % p-FNB | |
| --- | --- | --- | --- | --- |
| | Ex. V | Ex. VI | Ex. V | Ex. VI |
| 0.5 | 73.9 | 67.5 | 26.1 | 32.5 |
| 1.0 | 56.5 | 52.6 | 43.5 | 47.4 |
| 1.5 | 42.5 | 35.6 | 57.5 | 64.4 |
| 2.0 | 29.3 | 23.0 | 70.7 | 77.0 |
| 2.5 | 19.6 | 15.7 | 80.4 | 84.3 |
| 3.0 | 17.1 | 11.2 | 82.9 | 88.8 |
| 3.5 | 16.0 | 8.3 | 84.0 | 91.7 |
| 4.0 | 12.6 | 6.8 | 87.4 | 93.2 |

EXAMPLE VII

The experiment of Example IV was repeated in all essential details, except 14.7 g (0.254 mole) of potassium fluoride was used, and 39.6 g (0.508 mole) of dimethylsulfoxide was used. The results of the experiment are listed in the following table.

| Reaction Time (Hours) | Area % p-CNB | Area % p-FNB |
| --- | --- | --- |
| 0.5 | 73.0 | 27.0 |
| 1.0 | 59.6 | 40.4 |
| 1.5 | 43.8 | 56.2 |
| 2.0 | 34.4 | 65.6 |
| 2.5 | 21.2 | 78.8 |
| 3.0 | 14.3 | 85.7 |
| 3.5 | 8.9 | 91.1 |
| 4.0 | 7.1 | 92.9 |

EXAMPLES VIII, IX and X

The experiment of Example IV was repeated in all essential details, except 14.0 g (0.191 mole) of potassium fluoride was used, 29.7 g (0.381 mole) of dimethylsulfoxide was used, and the incremental amount of catalyst was varied. In Example VIII, 0.25 g of catalyst was added at thirty minute intervals after the first hour at the indicated reaction temperature, in Example IX, 0.35 g of catalyst was added at each thirty minute interval, and in Example X, 0.75 g of catalyst was added at each thirty minute interval. The results of the experiments are listed in the following table:

| Reaction Time (Hours) | Area % p-CNB | | | Area % p-FNB | | |
| --- | --- | --- | --- | --- | --- | --- |
| | Ex VIII | Ex IX | Ex X | Ex VIII | Ex IX | Ex X |
| 0.5 | 70.9 | 69.4 | 66.8 | 29.1 | 30.6 | 33.2 |
| 1.0 | 55.7 | 57.0 | 52.8 | 44.3 | 43.0 | 47.2 |
| 1.5 | 42.5 | 43.9 | 36.5 | 57.5 | 56.1 | 63.5 |
| 2.0 | 31.5 | 34.6 | 23.1 | 68.5 | 65.4 | 76.9 |
| 2.5 | 26.9 | 25.3 | 16.2 | 73.1 | 74.7 | 83.8 |
| 3.0 | 23.1 | 18.1 | 10.2 | 76.9 | 81.9 | 89.8 |

EXAMPLE XI

This example describes a scaled-up synthesis and recovery of p-fluoronitrobenzene, according to the method of the present invention.

Drying of Reagents

Potassium fluoride (110 g) was refluxed in 400 ml. of toluene, which was then removed by distillation. The potassium fluoride was then dried under vacuum.

Anhydrous dimethylsulfoxide was stored over molecular sieves for several months prior to use.

Aliquat ® 336 catalyst (50 g) was dissolved in 100 g of dimethylsulfoxide, to which was then added a few grams of activated alumina. The solution was stored for at least two hours prior to use.

Anhydrous p-chloronitrobenzene was used as purchased.

Reaction

Potassium fluoride (100 g), p-chloronitrobenzene (200 g), dimethylsulfoxide (297 g) and 30 g of the Aliquat ® 336 catalyst solution described above were mixed in a vessel purged with nitrogen and heated to 170°–175° C. After the initiation of the reaction, additional catalyst solution was added in 15 g increments at 30 minute intervals for 4 hours. A nitrogen blanket was maintained over the mixture throughout the reaction. After the last addition of catalyst, the reaction mixture was maintained at 170°–175° C. for 2 hours. The reaction mixture was analyzed by gas chromatography at this point, and it contained no detectable p-chloronitrobenzene. Water (1500 ml.) was added to the reaction mixture and the liquid was placed in a separatory funnel. After separating the layers, the aqueous layer was extracted one time with 100 ml. of methylene chloride. The methylene chloride was removed by evaporation under vacuum, to yield 232.4 g of crude product. Gas chromatographic analysis indicated a yield of p-fluoronitrobenzene of 157.1 g (87.8%), with no detectable p-chloronitrobenzene.

I claim:

1. A method for producing a fluoronitrobenzene compound by reacting a corresponding chloronitrobenzene compound with a fluoride salt in an aprotic, polar, organic solvent under halide-exchange conditions, including an elevated reaction temperature of from about 120° C. to about 220° C., in the presence of a catalyzing amount of quaternary ammonium salt phase-transfer catalyst, which comprises adding said phase-transfer catalyst to the reaction mixture incrementally at a rate of from about 0.005 to about 0.1 mole per mole of chloronitrobenzene compound per hour during the course of the reaction.

2. The method of claim 1, wherein the phase-transfer catalyst is soluble in the polar organic solvent, and is a compound of the formula

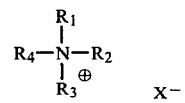

wherein each of $R_1$, $R_2$, $R_3$, and $R_4$ is an alkyl group of up to about 30 carbon atoms, provided that at least one of $R_1$–$R_4$ is an alkyl group of 5 to about 30 carbon atoms, and $X^-$ is an anion which dissociates from the ammonium ion in the polar organic solvent.

3. The method of claim 2, wherein each of $R_1$, $R_2$, $R_3$ and $R_4$ is an alkyl group of up to about 20 carbon atoms, provided that at least one of $R_1$–$R_4$ is an alkyl group of from about 8 to about 20 carbon atoms, and $X^-$ is an anion selected from the group consisting of fluoride, bromide, iodide, nitrate, and bisulfate.

4. The method of claim 1, wherein the catalyst is tricaprylmethylammonium chloride.

5. The method of claim 1, wherein an amount of catalyst is added to the reaction mixture in a molar ratio of catalyst to chloronitrobenzene compound from about 0.005:1 to about 0.1:1.

6. The method of claim 1, 2 or 3, wherein an initial amount of catalyst is added to the reaction mixture in a molar ratio of catalyst to chloronitrobenzene compound from about 0.01:1 to about 0.03:1, and during the course of the reaction, additional catalyst is added to the reaction mixture incrementally at a rate of from about 0.01 to about 0.03 mole per mole of chloronitrobenzene compound per hour.

7. The method of claim 1, 2, 3, 4, or 5 wherein the fluoronitrobenzene compound is selected from the group consisting of 2-fluoronitrobenzene, 2-fluoro-3-chloronitrobenzene, 4-fluoronitrobenzene, 2,4-difluoronitrobenzene, and 5-chloro-2,4-difluoronitrobenzene.

8. The method of claim 6, wherein the fluorointrobenzene compound is selected from the group consisting of 2-fluoronitrobenzene, 4-fluoronitrobenzene, 2,4- difluoronitrobenzene, and 5-chloro-2,4-difluoronitrobenzene.

9. The method of claim 1, 2, 3, 4, or 5, wherein the fluoronitrobenzene compound is 4-fluoronitrobenzene.

10. The method of claim 5, wherein the fluoronitrobenzene compound is 4-fluoronitrobenzene.

11. The method of claim 1, 2, 3, 4, or 5, wherein the halogen-exchange conditions include an elevated reaction temperature of from about 120° C. to about 220° C., the reaction mixture is substantially anhydrous; the polar organic solvent is dimethylsulfoxide, sulfolane, bis(2-methoxyethyl)ether, bis[2-(2-methoxyethoxy)ethyl]ether, hexamethylphosphoramide, N-methylpyrolidinone or dimethylformamide and the fluoride salt is an alkali metal fluoride selected from the group consisting of potassium fluoride, rubidium fluoride and cesium fluoride.

12. The method of claim 6, wherein the halogen-exchange conditions include an elevated reaction temperature of from about 120° C. to about 220° C., the reaction mixture is substantially anhydrous, the polar organic solvent is dimethylsulfoxide, sulfolane, bis(2-methoxyethyl)ether, bis[2-(2-methoxyethoxy)ethyl]ether, N-methylpyrolidinone, or dimethylformamide, and the fluoride salt is an alkali metal fluoride selected from the group consisting of potassium fluoride, rubidium fluoride, and cesium fluoride.

13. The method of claim 8, wherein the halogen-exchange conditions include an elevated reaction temperature of from about 120° C. to about 220° C.; the reaction mixture is substantially anhydrous; the polar organic solvent is dimethylsulfoxide, sulfolane, bis(2-methoxyethyl)ether, bis[2-(2-methoxyethoxy)ethyl]ether, hexamethylphosphoramide, N-methylpyrolidinone, or dimethylformamide; and the fluoride salt is finely divided potassium fluoride.

14. The method of claim 1, 2, 3, 4, or 5, wherein the halogen-exchange conditions include an elevated reaction temperature of from about 150° C. to about 180° C.; the reaction mixture contains less than about 5 wt. % water; the polar, organic solvent is dimethylsulfoxide or hexamethylphosphoramide; and the fluoride salt is finely divided potassium fluoride.

15. The method of claim 6, wherein the halogen-exchange conditions include an elevated reaction temperature of from about 150° C. to about 180° C; the reaction mixture contains less than about 5 wt. % water; the polar organic solvent is dimethylsulfoxide or hexamethylphosphoramide; and the fluoride salt is finely divided potassium fluoride.

16. The method of claim 9, wherein the halogen-exchange conditions include an elevated reaction temperature of from about 150° C. to about 180° C.; the reaction mixture contains less than about 5% water; the polar organic solvent is dimethylsulfoxide; the fluoride salt is finely divided potassium fluoride; and the reaction is conducted for from about 1 to about 6 hours.

* * * * *